US007785781B2

(12) United States Patent
Kozian et al.

(10) Patent No.: US 7,785,781 B2
(45) Date of Patent: Aug. 31, 2010

(54) METHOD OF DIAGNOSIS OF A PREDISPOSITION TO DEVELOP THROMBOTIC DISEASE AND ITS USES

(75) Inventors: Detlef Kozian, Hattersheim (DE); Matthias Herrmann, Hofheim (DE); Jean-Francois Deleuze, Combs la Ville (FR); Sylvain Ricard, Paris (FR); Sandrine Mace, Jouy-en-Josas (FR)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 412 days.

(21) Appl. No.: 10/592,692

(22) PCT Filed: Mar. 16, 2005

(86) PCT No.: PCT/EP2005/002761

§ 371 (c)(1), (2), (4) Date: May 8, 2007

(87) PCT Pub. No.: WO2005/095642

PCT Pub. Date: Oct. 13, 2005

(65) Prior Publication Data

US 2008/0038722 A1 Feb. 14, 2008

Related U.S. Application Data

(60) Provisional application No. 60/605,757, filed on Aug. 31, 2004.

(30) Foreign Application Priority Data

Mar. 29, 2004 (EP) .................................. 04007511

(51) Int. Cl.
*C12Q 1/68* (2006.01)
*C07H 21/02* (2006.01)

(52) U.S. Cl. .......................................... 435/6; 536/23.1

(58) Field of Classification Search ....................... None
See application file for complete search history.

(56) References Cited

OTHER PUBLICATIONS

Oury et al. Overexpression of the platelet P2X1 ion channel in transgenic mice generates a novel prothrombotic phenotype. Blood 101(10):3969-76, published online Jan. 9, 2003.*

GenBank accession No. AF177472.1 [online] Jun. 12, 2001 [retrieved on Mar. 18, 2009] retrieved from http://www.ncbi.nlm.nih.gov/nuccore/5901748.*

Oury et al. A natural dominant negative P2X1 receptor due to deletion of a single amino acid residue. The Journal of Biological Chemistry 275(30):22611-4, Jul. 28, 2000.*

Berry et al., Increase in expression of Psub2x1 receptors in the atria of patients suffering from dilated cariomyopathy, Electrophoresis, vol. 20, 1999, pp. 2059-2064.

Hou et al., Increase in Cardiac P2Xsub1 and P2Ysub2-Receptor mRNA Levels in Congestive Hear Failure, Life Sciences, vol. 65, No. 11, 1999, pp. 1195-1206.

Dhulipala et al., Regulation of human P2Xsub1 promoter activity by Beta helix-loop-helix factors in smooth muscle cells, Gene, vol. 269, No. 1-2, May 16, 2001, pp. 167-175.

Hechler et al., A Role of the Fast ATP-gated P2Xsub1 Cation Channel in Thrombosis of Small Arteries In Vivo, J. of Exp. Med., vol. 198, No. 4, Aug. 18, 2003, pp. 661-667.

Li et al., Association of a Polymorphism in the P2Xsub 7 Gene with Tuberculosis in a Gambian Population, J. of Infectious Diseases, vol. 186, No. 10, Nov. 15, 2002, pp. 1458-1462.

* cited by examiner

*Primary Examiner*—Samuel Woolwine

(57) ABSTRACT

The present invention refers to a method of diagnosis of a predisposition to develop thrombotic disease, to test systems and their use for the diagnosis of a predisposition to develop thrombotic disease, to a $P_2X_1$ promoter variant and its use for screening for an anti-thrombotic agent, and to methods for identifying an individual that can be prophylactically or therapeutically treated with an anti-thrombotic agent, or for adapting a therapeutic or prophylactic dose of an anti-thrombotic agent.

9 Claims, No Drawings

METHOD OF DIAGNOSIS OF A PREDISPOSITION TO DEVELOP THROMBOTIC DISEASE AND ITS USES

CROSS REFERENCE TO RELATED APPLICATIONS

This application is a §371 National Filing of International Patent Application No. PCT/EP2005/002761, filed Mar. 16, 2005, which claims priority under 35 U.S.C. §119(e) to U.S. Provisional Application No. 60/605,757, filed Aug. 31, 2004; and which claims priority under 35 U.S.C. §119(a) to European Patent Application No. 04007511.1, filed on Mar. 29, 2004, the disclosures of which are incorporated herein in their entirety.

The present invention refers to a method of diagnosis of a predisposition to develop thrombotic disease, to test systems and their use for the diagnosis of a predisposition to develop thrombotic disease, to a $P_2X_1$ promoter variant and its use for screening for an anti-thrombotic agent, and to methods for identifying an individual that can be prophylactically or therapeutically treated with an anti-thrombotic agent, or for adapting a therapeutic or prophylactic dose of an anti-thrombotic agent.

Thrombotic disease, such as peripheral vascular disease (PVD), stroke, and myocardial infarction, can be caused by arteriosclerotic plaques or by blood platelet aggregates. The risk of an individual to develop thrombotic disease appears to be influenced, at least in part, by a genetic predisposition. However, the underlying genetic factors are not yet completely known (Arterioscler Thromb Vasc Biol 24:1-14, 2004).

At present, only a small number of diagnostic tests are available for determining the predisposition of an individual for thrombotic disease. (Saffroy R, Lemoine A, Haas p, Tindiliere F, Marion S, Debuire B. Rapid automated simultaneous screening of (G1691 A) Factor V, (G20210A) prothrombin, and (C677T) methylenetetrahydrofolate reductase variants by multiplex PCR using fluorescence scanning technology. Genet Test. 2002 Fall; 6(3):233-6).

However, the known tests all have the problem, that the risk of thrombotic disease of an individual cannot be reliably determined. Therefore there is a need for new test systems which allow to reliably determine the predisposition of an individual of thrombotic disease, in particular the risk of PVD, of stroke, or of myocardial infarction.

It is an object of the present invention to provide more reliable methods of diagnosis of a predisposition of an individual to develop thrombotic disease. In particular, it is desirable to provide a test system for convenient handling of a suitable method of diagnosis, to provide a method and a test system for screening for new anti-thrombotic agents, to provide a method of identifying an anti-thrombotic agent for the prophylactic or therapeutic treatment of an individual having a predisposition to develop thrombotic disease, and to provide a method of adapting a therapeutic or prophylactic dose of an anti-thrombotic agent.

According to a first aspect of the present invention, the object is solved by providing a method of diagnosis of a predisposition to develop thrombotic disease, wherein the method comprises: (a) determining the sequence of at least one allele of the $P_2X_1$ promoter at least at one of the positions 304, 764, 838, or 1002 of SEQ ID NO: 1, and/or (b) determining the amount of the $P_2X_1$ protein in a tissue sample obtained from an individual.

In the present invention, it has surprisingly been found, that the $P_2X_1$ promoter occurs in humans in the form of $P_2X_1$ promoter variants comprising sequence variations at the above-identified positions, which are closely correlated to a predisposition of their carriers to develop various forms of thrombotic disease. The present invention is based on the study performed with 1400 patients, which is, due to the high number of patients, very meaningful. Therefore, the present invention provides for the first time a reliable method of diagnosis of a predisposition to develop thrombotic disease. Preferred embodiments of the method of diagnosis of the invention refer to the diagnosis of particular forms of thrombotic disease which are correlated to the presence of particular $P_2X_1$ promoter variants.

The variations of individual nucleotides in the $P_2X_1$ promoter as claimed in the present invention occur with a high frequency in a given population, in particular with a frequency >1%, and can therefore be classified as so-called single-nucleotide polymorphisms (SNPs). Therefore, they are well suited as diagnostic markers of a predisposition of an individual for developing thrombotic disease.

The single nucleotide polymorphisms (SNPs) in the $P_2X_1$ promoter have an impact on the amount of the $P_2X_1$ protein produced in the respective individual. Therefore, according to the present invention, an altered amount of the $P_2X_1$ protein in a tissue sample is the reliable marker for the predisposition to develop thrombotic disease.

The $P_2X_1$ receptor is a member of the so-called ATP-gated ion channels of the $P_2X$ receptor family. It is found in a multitude of human tissues and cells, for example in neurons, smooth muscle cells, and blood platelets (Gene 2001, Vol 269:167-175; Thromb Haemost 1998, Vol 103:858-866). The amino acid sequence of the $P_2X_1$ receptor is available under the Accession Number S71927 at the NCBI protein database.

In blood platelets, $P_2X_1$ is involved in the mobilization of calcium ions and in the initiation of the aggregation of platelets (J Biol Chem 1998, Vol 273:2024-2029). Sporadically, mutations in the gene of the $P_2X_1$ receptor leading to abnormally strong hemorrhage in their carriers have been described (J Biol Chem 2002, Vol 275:22611-22614). In smooth muscle cells the $P_2X_1$ receptors are responsible for vasoconstriction. In endothelium cells the activation of $P_2X_1$ by ATP leads to the liberation of prostacyclin and nitrogen monoxide (NO), which exert vasodilatory and antiproliferative effects on smooth muscle cells (TIPS 1998, Vol 19:99-107).

Recently, the sequence of the promoter of the $P_2X_1$ gene and its deletion mutants have been described (Gene 2001, Vol 269:167-175; Accession Number AF177472, NCBI Nucleotide Database). It has been shown that certain regions of the promoter contribute pivotally to the transcription of the $P_2X_1$ mRNA. Furthermore, it is known that the $P_2X_1$ protein is involved in thrombotic processes (J Exp Med 198(4):661-7, 2003).

In the present invention, reference to positions within the nucleotide sequence of the $P_2X_1$ promoter is made referring to SEQ ID NO:1, which corresponds to the sequence available under the Accession Number AF177472 at the NCBI Nucleotide Database. Preferably, the $P_2X_1$ protein comprises the amino acid sequence according to SEQ ID NO:2, which is available under the Accession Number S71927 at the NCBI Protein Database.

In the present invention, previously unknown variations of individual nucleotides in the $P_2X_1$ promoter have been observed, which are correlated to the predisposition of an individual to develop thrombotic disease. These variations comprise the variation from C to T at position 304, from G to C at position 764, from T to G at position 838, or from T to C at position 1002 of SEQ ID NO:1. The order of citation of the individual nucleotides, e.g. "from C to T at position 304"

indicates the variation from the more frequently occurring base at a given position to the less frequently observed base at the same position.

According to the present invention, an individual may comprise 1, 2, 3 or 4 of the variations in the $P_2X_1$ promoter at the positions 304, 764,838 or 1002 of SEQ ID NO:1, may comprise no variation at the positions 304, 764, 838 or 1002 of SEQ ID NO:1, or may comprise any combination of either the bases C or T at position 304, G or C at position 764, T or G at position 838, or T or C at position 1002 of SEQ ID NO:1 on either one or both alleles of the $P_2X_1$ promoter.

In the present invention, diagnosis of a predisposition to develop thrombotic disease comprises the determination of the risk of an individual to develop thrombotic disease, and/or the diagnosis of acute or chronic thrombotic disease. Thrombotic disease comprises any form of thrombosis, in particular any form of intravital blood plug formation in arteries or veins and any associated clinical symptoms in any part of the human or animal body, in particular in any organ or member. A blood plug comprises in particular aggregates of blood platelets and/or plaque material derived from arteriosclerotic plaques. Thrombotic disease preferably comprises peripheral vascular disease (PVD), myocardial infarction, preferably early myocardial infarction, and stroke, in particular comprising transitory ischemic attack (TIA) and/or prolonged reversible ischemic neurological deficit (PRIND). PVD comprises in particular a common circulation problem in which the arteries that carry blood to the legs or arms become narrowed or clogged, and which is sometimes called peripheral arterial disease, or PAD. Many people also refer to the condition as "hardening of the arteries." Early myocardial infarction preferably refers to any form of myocardial infarction occurring in people or animals at any age prior to old age.

The methods of diagnosis of the invention preferably refer to in vitro methods of diagnosis, wherein a tissue sample is used, which has been removed from the body of an individual prior to executing the method of diagnosis of the invention. Further preferred embodiments of the invention refer to in vivo methods of diagnosis, preferably wherein a tissue sample located within the body of an individual is used in in-situ methods of diagnosis.

In the present invention, a tissue sample comprises preferably cells, such as blood cells, in particular blood platelets, red and/or white blood cells, smooth muscle cells, striated muscle cells, epithelial cells of any epithelium, connective tissue cells of any connective tissue, neurons, tissue samples of the skin, mucosal tissue samples, tissue samples of any organ, and any body fluids, in particular whole blood, or any blood fraction, liquor, lymph, urine, saliva, and semen.

In the present invention, an individual comprises any vertebrate animal, preferably any mammal, preferably a human, of any age or sex, in particular a new-born, child, adolescent, adult, or senescent human or animal, any human or animal germ-line cell, a human or animal oocyte or spermatocyte, a human or animal fertilized oocyte, any human or animal being prior to birth, in particular any human or animal embryo or fetus.

In a preferred embodiment of the method of diagnosis of a predisposition to develop thrombotic disease, the presence in a tissue sample from an individual of at least one allele of the $P_2X_1$ promoter comprising a variation from C to T at position 304 of SEQ ID NO:1 is indicative of an increased risk of peripheral vascular disease (PVD). Preferably, the presence of the variation from C to T at position 304 on both alleles of the $P_2X_1$ promoter is indicative of a further increased risk of PVD.

In a further preferred embodiment, the presence in a tissue sample of at least one allele of the $P_2X_1$ promoter comprising a variation from G to C at position 764 of SEQ ID NO:1 is indicative of an increased risk of PVD. Preferably, the presence of the variation from G to C at position 764 on both alleles of the $P_2X_1$ promoter is indicative of a further increased risk of PVD.

In further preferred embodiments, the presence of the variation from C to T at position 304 of SEQ ID NO:1 on both alleles of the $P_2X_1$ promoter, or the presence of the variation from G to C at position 764 of SEQ ID NO:1 on both alleles of the $P_2X_1$ promoter is indicative of a reduced risk of stroke, in particular of a reduced risk of transitory ischemic attack (TIA) or of prolonged reversible ischemic neurological deficit (PRIND).

In further preferred embodiments, the presence of C at position 304 of SEQ ID NO:1 instead of a T on at least one allele of the $P_2X_1$ promoter, or the presence of G at position 764 of SEQ ID NO:1 instead of C on at least one allele of the $P_2X_1$ promoter is indicative of an increased risk of stroke.

In a further preferred embodiment, the presence in a tissue sample of at least one allele of the $P_2X_1$ promoter comprising a variation from T to G at position 838 of SEQ ID NO:1 is indicative of a reduced risk of early myocardial infarction. Furthermore, the presence in a tissue sample of at least one allele of the P2X1 promoter comprising a T at position 838 of SEQ ID NO:1 is indicative an increased risk of premature myocardial infarction. Preferably, the presence of the variation from T to G at position 838 on both alleles of the $P_2X_1$ promoter is indicative of a further reduced risk of early myocardial infarction.

In the present invention, the risk of an early myocardial infarction is preferably the risk of women having less than 55 years of age or of men having less than 60 years of age of suffering a myocardial infarction.

In a further preferred embodiment, the presence in a tissue sample of at least one allele of the $P_2X_1$ promoter comprising the variation from T to C at position 1002 of SEQ ID NO:1 is indicative of an increased risk of PVD. Preferably, the presence of the variation from T to C at position 1002 on both alleles of the $P_2X_1$ promoter is indicative of a further increased risk of PVD.

In further preferred embodiments, the sequence of the $P_2X_1$ promoter is determined at more than one position, preferably at two, at three, or at all positions 304, 764, 838, or 1002 of SEQ ID NO:1. Preferably, the sequence of both alleles of the $P_2X_1$ promoter is determined at one, two, three or all positions 304, 764, 838, or 1002 of SEQ ID NO:1.

Preferably, the sequence of the $P_2X_1$ promoter or of fragments thereof comprising at least one of positions 304, 764, 838, or 1002 of SEQ ID N 0:1 is determined using any method for the sequence analysis of nucleic acids, in particular any DNA sequencing protocol based on the DNA sequencing protocol according to Sanger (Current Protocols in Molecular Biology, edited by Fred M. Ausubel, Roger Brent, Robert E. Kingston, David D. Moore, J. G. Seidman, John A. Smith, Kevin Struhl; Looseleaf: 0-471-650338-X; CD-ROM: 0-471-30661-4), in particular using radioactively labeled nucleotides or using nucleotides labeled with a fluorescent dye, in particular involving a polymerase chain reaction (PCR), or using a chemical sequencing method (Pyrosequencing: an accurate detection platform for single nucleotide polymorphisms, Hum Mutat. 2002 May; 19(5):479-85), in particular using pyrosequencing (Pyrosequencing for SNP genotyping, Methods Mol Biol. 2003; 212:189-95; Comparison of GenFlex Tag array and Pyrosequencing in SNP genotyping, J Mol Diagn. 2003 November; 5(4):243-9; Microarrays and genetic epidemiology: a multipurpose tool for a multifaceted field. Genet Epidemiol. 2002 June; 23(1):4-20, review), or using mass spectrometry for the analysis of a nucleic acid sequence (A novel MALDI-TOF based methodology for genotyping single nucleotide polymorphisms, Nucleic Acids Res. 2003 Dec. 15; 31(24):e155; Digital genotyping using molecular affinity and mass spectrometry, Nat Rev Genet. 2003 December; 4(12):1001-8).

In addition, the sequence of the $P_2X_1$ promoter or of fragments thereof comprising at least one of the positions 304, 764, 838, or 1002 of SEQ ID NO: 1 can be determined using any sequence-specific nucleic acid detection method allowing to detect single-nucleotide variations, in particular any such method involving complementary base pairing. For example, the $P_2X_1$ promoter variants of the invention can be detected in a polymerase chain reaction (PCR) using oligonucleotide primers allowing the amplification of a $P_2X_1$ promoter fragment only if either C or T is present at position 304, either G or C is present at position 764, either T or G is present at position 838, and/or either T or C is present at position 1002 of SEQ ID NO:1. Methods for performing PCR are known in the art (Current Protocols in Molecular biology; edited by Fred M. Ausubel et al., supra). Further, a so-called TaqMan analysis can be used for the detection of the $P_2X_1$ promoter variants of the invention (PNAS USA, 88: 7276-7280; Nucl Acid Res, 21: 3761-3766). Further, a DNA-microarray allowing the detection of a $P_2X_1$ promoter fragment only if either C or T is present at position 304, either G or C is present at position 764, either T or G is present at position 838, and/or either T or C is present at position 1002 of SEQ ID NO:1 can be used, which the skilled person readily provides (Microarrays and genetic epidemiology: a multipurpose tool for a multifaceted field, Genet Epidemiol. 2002 June; 23(1):4-20; High-density genechip oligonucleotide probe arrays, Adv Biochem Eng Biotechnol. 2002; 77:21-42). Further, Southern hybridization assays using nucleic acid probes allowing the detection of the single-nucleotide polymorphisms of the $P_2X_1$ promoter variants of the invention may be used.

Preferably, the sequence of the $P_2X_1$ promoter is determined in a DNA sequencing protocol or in a method involving a polymerase chain reaction, preferably in a TaqMan PCR analysis, using at least one oligonucleotide comprising SEQ ID NO:3 or SEQ ID NO:4 for determining the sequence of the $P_2X_1$ promoter at position 304 of SEQ ID NO:1, using at least one oligonucleotide comprising SEQ ID NO:5 or SEQ ID NO:6 for determining the sequence of the $P_2X_1$ promoter at position 764 of SEQ ID NO:1, using at least one oligonucleotide comprising SEQ ID NO:7 or SEQ ID NO:8 for determining the sequence of the $P_2X_1$ promoter at position 838 of SEQ ID NO:1, and/or using at least one oligonucleotide comprising SEQ ID NO:9 or SEQ ID NO:10 for determining the sequence of the $P_2X_1$ promoter at position 1002 of SEQ ID NO:1.

SEQ ID NO:3 corresponds to position 62490-62507 of the NCBI sequence AC005940.3.

SEQ ID NO:4 is the antisense strang to position 472-289 of SEQ ID NO:1.

SEQ ID NO:5 corresponds to position 618-635 in SEQ ID NO:1.

SEQ ID NO:6 is the antisense strang to position 775-784 of SEQ ID NO:1.

SEQ ID NO:7 corresponds to position 818-837 in SEQ ID NO:1.

SEQ ID NO:8 is the antisense strang to position 1003-1022 of SEQ ID NO:1

SEQ ID NO:9 corresponds to position 818-837 in SEQ ID NO:1.

SEQ ID NO:10 is the antisense strang to position 1003-1022 in SEQ ID NO:1.

In a further preferred embodiment of the method of the invention of diagnosis of a predisposition to develop thrombotic disease, an altered amount of the $P_2X_1$ protein in a tissue sample is indicative of the predisposition to develop thrombotic disease.

In the present invention, determining the amount of the $P_2X_1$ protein in a tissue sample preferably comprises determining its amount or determining its presence in a tissue sample. Preferably, determining the amount of the $P_2X_1$ protein in a tissue sample comprises any method of detecting an individual protein, for example a Western analysis or an ELISA assay using an anti-$P_2X_1$ antiserum or an anti-$P_2X_1$ antibody, in particular using a monoclonal anti-$P_2X_1$ antibody or an anti-$P_2X_1$ antibody fragment, in particular $P_2X_1$ protein in a tissue sample using a single-chain antibody or an enzymatically or recombinantly produced antibody fragment (Current Protocols in Immunology; edited by: John E. Coligan, Ada M. Kruisbeek, David H. Margulies, Ethan M. Shevach, Waren Strober; Looseleaf: 0-471-52276-7; CD-ROM: 0371-30660-6). The invention encompasses the use of any anti-$P_2X_1$ antiserum or anti-$P_2X_1$ antibody, in particular any monoclonal anti-$P_2X_1$ antibody or an anti-$P_2X_1$ antibody fragment, in particular any single-chain antibody or enzymatically or recombinantly produced antibody fragment in the methods and test systems of the invention.

In preferred embodiments, the amount of the $P_2X_1$ mRNA is indicative of the amount of the $P_2X_1$ protein. Preferably, the amount of the $P_2X_1$ protein is determined by measuring the amount of the $P_2X_1$ mRNA. Preferably, the presence of the $P_2X_1$ mRNA is indicative of the presence of the $P_2X_1$ protein. Preferably, the $P_2X_1$ mRNA in the sense as used herein comprises the complementary sequence to at least part of the $P_2X_1$ promoter and/or encompasses at least part of the coding region of the $P_2X_1$ gene. Preferably, the amount of a precursor mRNA or of the mature mRNA or of a fragment thereof is determined. Preferably, the amount or presence of the mRNA is determined in a Northern analysis (Current Protocols in Molecular Biology; edited by Fred M. Ausubel et al., supra), in a PCR analysis comprising an initial step of reverse transcribing the RNA molecule, in a differential display analysis (Comparative gene-expression analysis; Trends Biotechnol. 1999 February; 17(2):73-8), or in a representational difference analysis (Comparative gene-expression analysis; Trends Biotechnol. 1999, supra).

In further preferred embodiments, the activity of the $P_2X_1$ protein in a tissue sample is indicative of its amount. Preferably, the activity of the $P_2X_1$ protein is determined in a $P_2X_1$ activity assay (Journal Biol. Chemistry, published Dec. 29, 2003 ahead of publishing as Manuscript No M308964200). Preferably, the activity of the $P_2X_1$ protein is determined in a human or animal cell.

According to a further aspect of the present invention, the variations in the $P_2X_1$ promoter of the present invention allow to provide a test system for the convenient determination of a predisposition to develop thrombotic disease. Thus, a further aspect of the present invention refers to a test system comprising at least one nucleic acid probe or oligonucleotide for determining the sequence of the $P_2X_1$ promoter at position 304, preferably for detecting either C or T at position 304, for determining the sequence of the $P_2X_1$ promoter at position 764, preferably for detecting either G or C at position 764, for determining the sequence of the $P_2X_1$ promoter at position 838, preferably for detecting either T or G at position 838, or for determining the sequence of the $P_2X_1$ promoter at position 1002, preferably for detecting either T or C at position 1002 of SEQ ID NO:1 in a tissue sample obtained from an individual.

Preferably, the oligonucleotide is at least one PCR primer, preferably a set of PCR §0 primers is provided, which allows to amplify a $P_2X_1$ promoter fragment only if either C or T is present at position 304, either G or C is present at position 764, either T or G is present at position 838, and/or either T or C is present at position 1002 of SEQ ID NO:1. The skilled person readily provides such an oligonucleotide or set of PCR primers (Current Protocols in Molecular Biology; edited by Fred M. Ausubel et al., supra).

In a preferred embodiment, the test system comprises at least one oligonucleotide comprising SEQ ID NO:3 or SEQ ID NO:4 for determining the sequence of the $P_2X_1$ promoter at position 304 of SEQ ID NO:1, at least one oligonucleotide comprising SEQ ID NO:5 or SEQ ID NO:6 for determining the sequence of the $P_2X_1$ promoter at position 764 of SEQ ID NO:1, at least one oligonucleotide comprising SEQ ID NO:7 or SEQ ID NO:8 for determining the sequence of the $P_2X_1$ promoter at position 838 of SEQ ID NO:1, and/or at least one oligonucleotide comprising SEQ ID NO:9 or SEQ ID NO:10 for determining the sequence of the $P_2X_1$ promoter at position 1002 of SEQ ID NO:1.

In a further preferred embodiment, the test system comprises a DNA-microarray, which preferably allows the detection of a $P_2X_1$ promoter fragment only if C is present at position 304, only if T is present at position 304, only if G is present at position 764, only if C is present at position 764, only if T is present at position 838, only if G is present at position 838, only if T is present at position 1002 and/or only if C is present at position 1002 of SEQ ID NO:1, which the skilled person readily provides (Microarrays and genetic epidemiology: a multipurpose tool for a multifaceted field, Genet Epidemiol. 2002 June; 23(1):4-20; High-density genechip oligonucleotide probe arrays, Adv Biochem Eng Biotechnol. 2002; 77:21-24).

In a further preferred embodiment, the test system comprises a labeled nucleic acid probe for use in a Southern hybridization assay, which allows the detection of a $P_2X_1$ promoter fragment only if C is present at position 304, only if T is present at position 304, only if G is present at position 764, only if C is present at position 764, only if T is present at position 838, only if G is present at position 838, only if T is present at position 1002 and/or only if C is present at position 1002 of SEQ ID NO:1. The skilled person is able to perform such experiments (Current Protocols in Molecular Biology; edited by Fred M. Ausubel et al., supra).

Preferably, the nucleic acid probe is radioactively labeled, fluorescently labeled, or is immunologically detectable, in particular is digoxygenin-labeled (Roche Diagnostics GmbH, Mannheim).

Still a further aspect of the present invention refers to the use of the above-mentioned test system comprising at least one nucleic acid probe or oligonucleotide for the diagnosis of a predisposition to develop thrombotic disease. With respect to the use of the test system, the embodiments defined above for the method of the invention of diagnosis of a predisposition to develop thrombotic disease also apply.

A further aspect of the present invention refers to a test system comprising at least one anti-$P_2X_1$ antiserum, anti-$P_2X_1$ antibody, or anti-$P_2X_1$ antibody-fragment for determining the presence, preferably the amount, of the $P_2X_1$ protein in a tissue sample obtained from an individual.

Preferably the test system comprises at least one monoclonal anti-$P_2X_1$ antibody or an anti-$P_2X_1$ antibody fragment, in particular a single-chain antibody or an antibody fragment, preferably an enzymatically or recombinantly produced single-chain antibody or an antibody fragment (references). Preferably, the test system of the invention encompasses any anti-$P_2X_1$ antiserum or anti-$P_2X_1$ antibody, in particular any monoclonal anti-$P_2X_1$ antibody or any anti-$P_2X_1$ antibody fragment, preferably any enzymatically or recombinantly produced single-chain antibody or an antibody fragment.

In the present invention, the $P_2X_1$ protein preferably comprises the amino acid sequence according to SEQ ID NO:2, which is available under the Accession Number S71927 at the NCBI protein database.

Preferably, the amount of the $P_2X_1$ protein in a tissue sample is determined using any method of detecting the presence or measuring the amount of an individual protein, for example in a Western analysis or in an ELISA assay.

A further aspect of the invention refers to the use of the test system comprising at least one anti-$P_2X_1$ antiserum, anti-$P_2X_1$ antibody, or anti-$P_2X_1$ antibody-fragment for the diagnosis of a predisposition to develop thrombotic disease.

Further aspects of the present invention refer to the detection of new prophylactic and therapeutic compounds for thrombotic disease, with the help of the $P_2X_1$ promoter variants of the invention.

A further aspect of the present invention refers to a $P_2X_1$ promoter variant comprising a DNA fragment comprising at least one of the positions 304, 764, 838, and/or 1002 of SEQ ID NO:1. Preferably, the $P_2X_1$ promoter variant comprises T or C at position 304, C or G at position 764, T at position 838, and/or C at position 1002 of SEQ ID NO:1. Preferably, the $P_2X_1$ promoter variant comprises the regions of the $P_2X_1$ promoter, which have been shown to contribute to the transcription of the $P_2X_1$ mRNA (Gene 2001, Vol 269:167-175).

A further aspect of the present invention refers to a test system comprising the $P_2X_1$ promoter variant of the invention, wherein the promoter variant directs the synthesis of a detectable product.

A further aspect of the present invention refers to the use of the test system comprising the $P_2X_1$ promoter variant of the invention for screening for an anti-thrombotic agent. Preferably, an anti-thrombotic agent is identified by its ability to counteract the effect of a given $P_2X_1$ promoter variant as compared to a wild type $P_2X_1$ promoter.

According to a further aspect of the invention referring to the detection of new prophylactic and therapeutic compounds for thrombotic disease, wherein the $P_2X_1$ promoter variants of the invention are used with advantage, a method of screening for an anti-thrombotic agent is provided.

A further aspect of the present invention refers to a method of screening for an anti-thrombotic agent, wherein the method comprises the steps of: (a) providing a $P_2X_1$ promoter variant of the invention, preferably a $P_2X_1$ promoter variant comprising T or C at position 304, C or G at position 764, T at position 838, or C at position 1002 of SEQ ID NO:1, (b) bringing the $P_2X_1$ promoter variant into contact with a test compound, and (c) determining the activity of the $P_2X_1$ promoter variant.

Preferably, an anti-thrombotic agent is an active agent for the prophylaxis or the treatment of thrombotic disease, preferably of PVD, stroke, preferably TIA, PRIND, and/or myocardial infarction, preferably early myocardial infarction.

In further preferred embodiments, the method of screening is adapted to a high-throughput screening of test compounds.

Preferably, the method involves determining the activity of the $P_2X_1$ promoter variant in the presence of a test compound, and comparing it to the activity of the $P_2X_1$ promoter variant in the absence of the test compound. Preferably, the method involves the use of the test system of the invention for screening for an anti-thrombotic agent, as described herein.

A test compound is preferably a small molecule which is a candidate for an effector molecule enhancing or inhibiting the activity of a component of the transcriptional apparatus of a cell, and in particular a candidate for a small molecule effector interacting with a component of the basal transcription apparatus, in particular interacting with the general or basal transcription factors involved in the mechanics of binding to DNA and initiating transcription. Preferably, the test compound is any chemical compound, such as a naturally occurring compound or a chemically synthesized compound that is identical or similar to a naturally occurring compound, or any chemically synthesized compound that does not occur in nature.

A naturally occurring compound is preferably a compound that can be detected in or isolated from a multicellular or single-cell organism, in particular in an animal, a plant, a fungus, a yeast, a bacterium, or any other cell-containing organism, or in a virus. A chemically synthesized compound that does not occur in nature is preferably synthesized by combinatorial chemistry. Preferably, it comprises a lead structure derived from a naturally occurring compound, preferably from a candidate for an effector molecule which can bind to a transcription factor or component of the basal transcriptional apparatus of a cell.

Preferably, the test compound is a biochemical or chemical test compound, e.g. in the form of a chemical compound library. According to the present invention the term "chemical compound library" refers to a plurality of chemical compounds that have been assembled from any of multiple sources, including chemically synthesized molecules and natural products, or that have been generated by combinatorial chemistry techniques. Preferably, the test compound is any low-molecular weight compound.

Advantageously, a chemical compound library is especially suitable for high throughput screening. It may be comprised of chemical compounds of a particular structure or compounds of a particular creature such as a plant.

In a preferred embodiment, the activity of the $P_2X_1$ promoter comprising T at position 304 of SEQ ID NO:1, in particular in a cell comprising T on one or both alleles of the $P_2X_1$ promoter, is determined and compared to the activity of the $P_2X_1$ promoter comprising C at position 304, and an anti-thrombotic agent is identified as a test compound which reverses the effect of T at position 304 on the activity of the $P_2X_1$ promoter. Preferably, the thus identified anti-thrombotic agent can be used for the prevention or the therapy of peripheral vascular disease (PVD).

In a further preferred embodiment, the activity of the $P_2X_1$ promoter comprising C at position 304 of SEQ ID NO:1, in particular in a cell comprising C on one or both alleles of the $P_2X_1$ promoter, is determined and compared to the activity of the $P_2X_1$ promoter comprising T at position 304, and an anti-thrombotic agent is identified as a test compound which reverses the effect of C at position 304 on the activity of the $P_2X_1$ promoter. Preferably, the thus identified anti-thrombotic agent can be used for the prevention or the therapy of stroke, preferably of TIA or PRIND.

In a further preferred embodiment, the activity of the $P_2X_1$ promoter comprising C at position 764 of SEQ ID NO: 1, in particular in a cell comprising C on one or both alleles of the $P_2X_1$ promoter, is determined and compared to the activity of the $P_2X_1$ promoter comprising G at position 764, and an anti-thrombotic agent is identified as a test compound which reverses the effect of C at position 764 on the activity of the $P_2X_1$ promoter. Preferably, the thus identified anti-thrombotic agent can be used for the prevention or the therapy of PVD.

In a further preferred embodiment, the activity of the $P_2X_1$ promoter comprising G at position 764 of SEQ ID NO:1, in particular in a cell comprising G on one or both alleles of the $P_2X_1$ promoter, is determined and compared to the activity of the $P_2X_1$ promoter comprising C at position 764, and an anti-thrombotic agent is identified as a test compound which reverses the effect of G at position 764 on the activity of the $P_2X_1$ promoter. Preferably, the thus identified anti-thrombotic agent can be used for the prevention or the therapy of stroke, preferably of TIA or PRIND.

In a further preferred embodiment, the activity of the $P_2X_1$ promoter comprising T at position 838 of SEQ ID NO:1, in particular in a cell comprising T on one or both alleles of the $P_2X_1$ promoter, is determined and compared to the activity of the $P_2X_1$ promoter comprising G at position 838, and an anti-thrombotic agent is identified as a test compound which reverses the effect of T at position 838 on the activity of the $P_2X_1$ promoter. Preferably, the thus identified anti-thrombotic agent can be used for the prevention or the therapy of myocardial infarction, preferably of early myocardial infarction.

In a preferred embodiment, the activity of the $P_2X_1$ promoter comprising C at position 1002 of SEQ ID NO:1, in particular in a cell comprising C on one or both alleles of the $P_2X_1$ promoter, is determined and compared to the activity of the $P_2X_1$ promoter comprising T at position 1002, and an anti-thrombotic agent is identified as a test compound which reverses the effect of C at position 1002 on the activity of the $P_2X_1$ promoter. Preferably, the thus identified anti-thrombotic agent can be used for the prevention or the therapy of PVD.

A further aspect of the present invention refers to a method for the manufacture of a medicament comprising at least one anti-thrombotic agent for the prophylaxis or treatment of thrombotic disease, preferably of PVD, stroke, in particular TIA or PRIND, and or of myocardial infarction, preferably of early myocardial infarction, wherein the anti-thrombotic agent is detected using the $P_2X_1$ promoter variants of the invention, preferably wherein the anti-thrombotic agent is detected in the method of the invention of screening for an anti-thrombotic agent.

A further aspect of the present invention refers to a method of identifying an anti-thrombotic agent which can be used for the prophylactic or therapeutic treatment of an individual having a predisposition to develop thrombotic disease, comprising the steps of: (a) identifying an individual having a predisposition to develop thrombotic disease, using the method of the present invention for identifying an individual having a predisposition to develop thrombotic disease, and (b) identifying an anti-thrombotic agent for the treatment of said individual, using the method of the invention of screening for an anti-thrombotic agent.

Another aspect of the present invention refers to a method of adapting a therapeutic or prophylactic dose of an anti-thrombotic agent, comprising the steps of: (a) identifying an individual having a predisposition to develop thrombotic disease, using the method of the present invention for identifying an individual having a predisposition to develop thrombotic disease, (b) identifying an anti-thrombotic agent for the treatment of said individual, using the method of the present invention of screening for an anti-thrombotic agent, and (c) selecting a therapeutically or prophylactically effective dose of said anti-thrombotic agent for said individual.

In addition, the invention refers to any further uses of the $P_2X_1$ promoter variants of the invention, wherein thrombotic diseases or their predisposition is diagnosed, or treatments are provided.

A further aspect of the present invention refers to the use of the $P_2X_1$ promoter variants of the invention for the development of a method or test system for the diagnosis of a predisposition to develop thrombotic disease, a method or test system for screening for an anti-thrombotic agent, a method or test system for identifying an individual which can be treated with an anti-thrombotic agent, or a method or test system for adapting a therapeutic or prophylactic dose of an anti-thrombotic agent.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

Description of the Sequences

SEQ ID NO:1 comprises the DNA sequence of the $P_2X_1$ promoter available under the Accession No. AF177472 at the NCBI Nucleotide Database.

SEQ ID NO:2 comprises the amino acid sequence of the $P_2X_1$ protein, available under the Accession No. S71927 at the NCBI Protein Database.

SEQ ID NO:3 comprises the sequence of a first oligonucleotide for determining the sequence of the $P_2X_1$ promoter at position 304 of SEQ ID NO:1. SEQ ID NO:3 corresponds to position 62490-62507 of the NCBI sequence AC005940.3.

SEQ ID NO:4 comprises the sequence of a second oligonucleotide for determining the sequence of the $P_2X_1$ promoter at position 304 of SEQ ID NO:1, which is located in the 3'-direction relative to SEQ ID NO:3 on the complementary strand. SEQ ID NO:4 is the antisense strang to position 472-289 of SEQ ID NO:1.

SEQ ID NO:5 comprises the sequence of a first oligonucleotide for determining the sequence of the $P_2X_1$ promoter at position 764 of SEQ ID NO:1. SEQ ID NO:5 corresponds to position 618-635 in SEQ ID NO:1.

SEQ ID NO:6 comprises the sequence of a second oligonucleotide for determining the sequence of the $P_2X_1$ promoter at position 764 of SEQ ID NO:1, which is located in the 3'-direction relative to SEQ ID NO:5 on the complementary strand. SEQ ID NO:6 is the antisense strang to position 775-784 of SEQ ID NO:1.

SEQ ID NO:7 comprises the sequence of a first oligonucleotide for determining the sequence of the $P_2X_1$ promoter at position 838 of SEQ ID NO:1. SEQ ID NO:7 corresponds to position 818-837 in SEQ ID NO:1.

SEQ ID NO:8 comprises the sequence of a second oligonucleotide for determining the sequence of the $P_2X_1$ promoter at position 838 of SEQ ID NO:1, which is located in the 3'-direction relative to SEQ ID NO:7 on the complementary strand. SEQ ID NO:8 is the antisense strang to position 1003-1022 of SEQ ID NO:1.

SEQ ID NO:9 comprises the sequence of a first oligonucleotide for determining the sequence of the $P_2X_1$ promoter at position 1002 of SEQ ID NO:1. SEQ ID NO:9 corresponds to position 818-837 in SEQ ID NO: 1.

SEQ ID NO:10 comprises the sequence of a second oligonucleotide for determining the sequence of the $P_2X_1$ promoter at position 1002 of SEQ ID NO:1, which is located in the 3'-direction relative to SEQ ID NO:9 on the complementary strand. SEQ ID NO:10 is the antisense strang to position 1003-1022 in SEQ ID NO:1.

DESCRIPTION OF THE EXAMPLES

Abbreviations Used for the $P_2X_1$ Promoter Variants

The following abbreviations are used, wherein the indicated positions refer to the positions of the nucleotides in SEQ ID NO:1:

- $P_2X_1$ C304C refers to a group of persons carrying a cytidine (C) at position 304 on both alleles of the $P_2X_1$ gene. These persons are homocygous for this $P_2X_1$ variant.
- $P_2X_1$ C304T refers to a group of persons carrying a cytidine (C) at position 304 on one allele of the $P_2X_1$ gene and a thymidine (T) at position 304 on the other allele of the $P_2X_1$ gene. These persons are heterocygous for this $P_2X_1$ variant.
- $P_2X_1$ T304T refers to a group of persons carrying a thymidine (T) at position 304 on both alleles of the $P_2X_1$ gene. These persons are homocygous for this $P_2X_1$ variant.
- $P_2X_1$ G764G refers to a group of persons carrying a guanosine (G) at position 764 on both alleles of the $P_2X_1$ gene. These persons are homocygous for this $P_2X_1$ variant.
- $P_2X_1$ C764G refers to a group of persons carrying a cytidine (C) at position 764 on one allele of the $P_2X_1$ gene and carrying a guanosine (G) at position 764 on the other allele of the $P_2X_1$ gene. These persons are heterocygous for this $P_2X_1$ variant.
- $P_2X_1$ C764C refers to a group of persons carrying a cytidine (C) at position 764 on both alleles of the $P_2X_1$ gene. These persons are homocygous for this $P_2X_1$ variant.
- $P_2X_1$ T838T refers to a group of persons carrying a thymidine (T) at position 838 on both alleles of the $P_2X_1$ gene. These persons are homocygous for this $P_2X_1$ variant.
- $P_2X_1$ T838G refers to a group of persons carrying a thymidine (T) at position 838 on one allele of the $P_2X_1$ gene and a guanosine (G) at position 838 on the other allele of the $P_2X_1$ gene. These persons are heterocygous for this $P_2X_1$ variant.
- $P_2X_1$ G838G refers to a group of persons carrying a guanosine (G) at position 838 on both alleles of the $P_2X_1$ gene. These persons are homocygous for this $P_2X_1$ variant.

$P_2X_1$ T1002T refers to a group of persons carrying a thymidine (T) at position 1002 on both alleles of the $P_2X_1$ gene. These persons are homocygous for this $P_2X_1$ variant.

- $P_2X_1$ TI 002C refers to a group of persons carrying a thymidine (T) at position 1002 on one allele of the $P_2X_1$ gene and a cytidine (C) at position 1002 on the other allele of the $P_2X_1$ gene. These persons are heterocygous for this $P_2X_1$ variant.
- $P_2X_1$ C1002C refers to a group of persons carrying a cytidine (C) at position 1002 on both alleles of the $P_2X_1$ gene. These persons are homocygous for this $P_2X_1$ variant.

The four single-nucleotide polymorphisms (SNPs) identified in the $P_2X_1$ promoter regions were investigated in a group of 1404 patients, in order to determine the association of these genetic variations with the clinical symptoms of these patients.

Detection of Single-Nucleotide Polymorphisms (SNPs) by DNA Sequence Analysis

Genomic regions within the promoter of the $P_2X_1$ gene were amplified using the following oligonucleotide primers:

1. For the detection of the nucleotide variation from C to T at position 304 in the $P_2X_1$ promoter sequence, the following primers were used, which are derived from the sequence AC005940.3:
   AC005940.3 is the number of a sequence deposited in the NCBI database of a genomic clone, which comprises sequences upstream of the $P_2X_1$ promoter. Based on that sequence, it is possible to design an oligonucleotide which can be used for the amplification of that region which allows identification of $P_2X_1$ promoter variants at position 304. In contrast, AF177472.1 is the number of that sequence of the $P_2X_1$ gene which has been deposited in the NCBI database and which comprises the promoter region and parts of the coding region.

```
5'-GAAAAGCCCATGACACCC-3'
5'-CAACACGGGACAGAGAAC-3'
```

2. For the detection of the nucleotide variation from G to C at position 764 in the $P_2X_1$ promoter sequence, the following primers were used, which were derived from SEQ ID NO:1:

```
5'-GATGTGGTGCTGGTCTTG-3'

5'-GCTGGCATCTCTATCCCCCA-3'
```

3. For the detection of the nucleotide variation from T to G at position 838 in the $P_2X_1$ promoter sequence, the following primers were used, which were derived from SEQ ID NO:1:

```
5'-GGAACTCAGAGCCTCCTTCC-3'

5'-GGCAAGATGGAGCTCTGGCC-3'
```

4. For the detection of the nucleotide variation from T to C at position 1002 in the $P_2X_1$ promoter sequence, the following primers were used, which were derived from SEQ ID NO:1:

```
5'-GGAACTCAGAGCCTCCTTCC-3'

5'-GGCAAGATGGAGCTCTGGCC-3'
```

The genomic regions were amplified using the above-identified oligonucleotide primers in the PCR protocol indicated below.

The reagents used were from Applied Biosystems (Foster City, USA):

20 ng genomic DNA; 1 unit TaqGold DNA polymerase; 1× Taq polymerase buffer; 500 μM dNTPs; 2.5 mM $MgCl_2$; 200 nM of each amplification primer pair (sequences under 1. and 2.); $H_2O$ ad 5 μl.

PCR amplification program for genotyping

| | |
|---|---|
| 1 cycle comprising: | 95° C. for 10 min; |
| followed by 2 cycles, each comprising: | 95° C. for 30 sec, followed by 70° C. for 30 sec; |
| followed by 2 cycles, each comprising: | 95° C. for 30 sec, followed by 65° C. for 30 sec; |
| followed by 2 cycles, each comprising: | 95° C. for 30 sec, followed by 60° C. for 30 sec; |
| followed by 40 cycles, each comprising: | 95° C. for 30 sec, followed by 56° C. for 30 sec, followed by 72° C. for 30 sec; |
| followed by 1 cycle comprising: | 72° C. for 10 min, followed by 4° C. for 30 sec. |

PCR amplification program for sequencing

| | |
|---|---|
| 1 cycle comprising: | 96° C. for 2 min; |
| followed by 30 cycles, each comprising: | 96° C. for 10 sec, followed by 55° C. for 10 sec, followed by 65° C. for 4 min; |
| followed by 1 cycle comprising: | 72° C. for 7 min, followed by 4° C. for 30 sec. |

Analysis of the Sequencing Products

The sequences were first analyzed using the Sequence Analysis Software (Applied Biosystems, Foster City, USA) in order to obtain crude data. The crude data were processed using Phred, Phrap, Polyphred and Consed. Phred, Phrap, Polyphred and Consed are software written by Phil Green of the Washington University (http://www.genome.washington.edu).

Example

Results Obtained with a Group of 1404 Patients

TABLE 1

| | | n | % |
|---|---|---|---|
| Total | | 1404 | |
| Gender | Female | 406 | 28.9 |
| | Male | 998 | 71.1 |
| Age* | | 62.7 (30.0-90.7) | |
| BMI* (Body Mass Index) | | 27.8 (16.7-57.1) | |
| High blood pressure | | 834 | 59.4 |
| Smokers | | 923 | 65.7 |
| Angina pectoris | | 210 | 62.7 |
| Diabetics (ADA) | | 445 | 31.7 |
| Cardiac infarction | | 579 | 41.0 |
| CAD (>20% stenosis) | | 1087 | 78.8 |
| Stroke | | 106 | 7.5 |

*Medians and Quartiles (Q1-Q3)

TABLE 2

| | $P_2X_1$ C304C | $P_2X_1$ C304T | $P_2X_1$ T304T | not determined |
|---|---|---|---|---|
| Patients (n) | 674 | 596 | 119 | 15 |
| | $P_2X_1$ G764G | $P_2X_1$ G764C | $P_2X_1$ C764C | |
| Patients (n) | 685 | 595 | 119 | 5 |
| | $P_2X_1$ T838T | $P_2X_1$ T838G | $P_2X_1$ G838G | |
| Patients (n) | 1128 | 243 | 17 | 16 |
| | $P_2X_1$ T1002T | $P_2X_1$ T1002C | $P_2X_1$ C1002C | |
| Patients (n) | 410 | 669 | 299 | 17 |

TABLE 3

| | $P_2X_1$ genotype | | |
|---|---|---|---|
| | $P_2X_1$ C304C | $P_2X_1$ C304T | $P_2X_1$ T304T |
| PVD | 7.27% | 9.90% | 13.45% |
| Stroke/PRIND/TIA | 7.27% | 8.89% | 2.52% |
| | $P_2X_1$ G764G | $P_2X_1$ G764C | $P_2X_1$ C764C |
| PVD | 7.01% | 10.08% | 13.45% |
| Stroke/PRIND/TIA | 7.30% | 8.91% | 2.52% |
| | $P_2X_1$ T838T | $P_2X_1$ T838G | $P_2X_1$ G838G |
| Early myocardial infarction | 20.12% | 13.99% | 5.88% |
| | $P_2X_1$ T1002T | $P_2X_1$ T1002C | $P_2X_1$ C1002C |
| PVD | 5.73% | 9.72% | 11.04% |

In the analyzed group of patients an increased risk of PVD was observed, depending on the presence and the number of alleles comprising a T at position 304 or, respectively, the presence and the number of alleles comprising a C at position 764 in the promoter of the $P_2X_1$ gene. In addition, a reduced risk of stroke/PRIND/TIA was observed in patients carrying $P_2X_1$ T304T or $P_2X_1$ C764C. An increased risk for the occurrence of an early myocardial infarction (defined as myocardial infarction in women <55 years and men <60 years) depends on the presence and the number of alleles comprising a T at position 838 in the promoter of the $P_2X_1$ gene. Further, an increased risk for the occurrence of PVD depends on the presence and the number of alleles comprising a C at position 1002 in the promoter of the $P_2X_1$ gene. On the basis of these association analyses it can be concluded that genetic variations in the promoter region of the $P_2X_1$ gene have an important impact on the occurrence and the frequency of cardiovascular and thrombotic diseases.

The invention claimed is:

1. A method of determining predisposition to developing peripheral vascular disease in an individual comprising:

obtaining a tissue sample from the individual;

performing an assay on the sample to determine the sequence of at least one allele of the $P_2X_1$ promoter including one or more of the nucleotides at position 304, 764 or 1002 of SEQ ID NO:1;

wherein a T at position 304, a C at position 764, and/or a C at position 1002 indicates a predisposition to peripheral vascular disease.

2. A method of determining predisposition to developing stroke in an individual comprising:

obtaining a tissue sample from the individual;

performing an assay on the sample to determine the sequence of at least one allele of the $P_2X_1$ promoter including one or more of the nucleotides at position 304 or 764 of SEQ ID NO:1;

wherein a C at position 304 and/or a G at position 764 indicates a predisposition to stroke.

3. A method of determining predisposition to developing myocardial infarction in an individual comprising:

obtaining a tissue sample from the individual;

performing an assay on the sample to determine the sequence of at least one allele of the $P_2X_1$ promoter including the nucleotide at position 838;

wherein a T at position 838 indicates a predisposition to myocardial infarction.

4. The method of any one of claims 1-3, wherein the method further comprises determining an amount of the $P_2X_1$ protein.

5. The method of claim 4, wherein an anti-$P_2X_1$ antiserum, anti-$P_2X_1$ antibody or anti-$P_2X_1$ antibody fragment is used for determining the amount of the $P_2X_1$ protein.

6. The method of any one of claims 1-3, wherein the method further comprises determining the amount of $P_2X_1$ mRNA, wherein said amount of $P_2X_1$ mRNA is indicative of the amount of $P_2X_1$ protein.

7. The method of claim 6, wherein the amount of $P_2X_1$ mRNA is determined by a Northern analysis, by a PCR analysis comprising an initial step of reverse transcribing the mRNA, by a differential display analysis, or by a representational difference analysis.

8. The method of any one of claims 1-3, wherein the method further comprises determining the amount of $P_2X_1$ activity, wherein said amount of $P_2X_1$ activity is indicative of the amount of $P_2X_1$ protein.

9. The method of claim 8, wherein the activity of the $P_2X_1$ protein is determined in a human or animal cell.

* * * * *

UNITED STATES PATENT AND TRADEMARK OFFICE

CERTIFICATE OF CORRECTION

PATENT NO. : 7,785,781 B2
APPLICATION NO. : 10/592692
DATED : August 31, 2010
INVENTOR(S) : Detlef Kozian et al.

It is certified that error appears in the above-identified patent and that said Letters Patent is hereby corrected as shown below:

In column 7, line 8, after "PCR" delete "§0".

In column 12, line 49, delete "TI 002C" and insert -- T1002C --, therefor.

Signed and Sealed this
Eighth Day of February, 2011

David J. Kappos
*Director of the United States Patent and Trademark Office*

SEQUENCE LISTING

```
<160> NUMBER OF SEQ ID NOS: 10

<210> SEQ ID NO 1
<211> LENGTH: 1506
<212> TYPE: DNA
<213> ORGANISM: Homo sapiens

<400> SEQUENCE: 1

ggattgatta attgacaagg agagactgac ctgggtgctg gaaggggcca tgggcagcct     60

tctgtgggtg acccccattc agacaggctg ccgggattcc cagccccagg gcctggctcc    120

tgcccagagc acttccagct catggctcgc cagcaagaag actccttatc agccttaagg    180

gtggggcggc tccgacgaca gggccgtggg ggctcgccag ggaggcccct gcttccagct    240

tgaacctcca gtaccacccc gggtgagctt gggcaactca tttctcttct ctgagcttgg    300

tttcctcatc ttcaaaacga ggggtggggc tggggaggcc tccagctctg aggagccaac    360

gtgggaccct ctgcccaccc caaacccctg tgttcagggc ccgagctggg ggtgggaagg    420

gaaggcaggg actgcagagg tgctgtgccc ccgactcatt gggggcctcc agttctctgt    480

cccgagttgc tgagacccat cccctgtgag cctcgaccta gaaggaacag ccccttattac   540

cccaatttac agatgaggca acaggctcgg agaggcaagg tgacacccag cccccacagc    600

caagaagtgg cagagccagg gatctccgag gtcaggctct ctcggctggt cttgggcccc    660

ccatggcacc ggtgacggat gtggtgctgg tcttggctgg gcacctgcca cctctctccc    720

tctgatggtg gcccccggca ggacagacag tgggagagga gaggtggggg atagagatgc    780

cagctcagca ccgaggttga ccgggcacgg ccaggctgga actcagagcc tccttcctct    840

ctgccttgct cgctgcagac ccccagggac gaagcagcca accctggtgg gggagggtgg    900

agggtggtgg atggggctgg ggatggaggt ctcattttgg cagtggaggg gagtcgcggg    960

gagtccccta atctgaggag actccagctt cccccaggcc ctggccagag ctccatcttg   1020

ccaggttttg gggggaggat aacttgagga gtcgactgag agctttatct ttgcccctgt   1080

gacgggtggc ctgtggtttc ctgccaacaa ctcctgtttc cggaggccca acaaggccca   1140

cgcagagcca ggaggggcag tggggctggg cctgggtggc cccaccagcc ccgccccatc   1200
```

-continued

```
tatctttggg aatttatttg tccatgggcg aggctggcct gcagtctgtt gccttccagg   1260

ggccaagagc tgctctgatc acccagggat tctctctcca acccaagtgc ctccagctga   1320

cctctggctc ctgtcctctg gctccacctg caccgccctg ctcttcctaa ggggccagga   1380

agcccccaga agctctacca tcgacgtggg tggtggcacc cggctcaccc tgagagcaga   1440

ggccgtgcag gggctcagt tctgagcccc agccggccca ccatggcacg gcggttccag   1500

gaggag                                                              1506


<210> SEQ ID NO 2
<211> LENGTH: 399
<212> TYPE: PRT
<213> ORGANISM: Homo sapiens

<400> SEQUENCE: 2

Met Ala Arg Arg Phe Gln Glu Glu Leu Ala Ala Phe Leu Phe Glu Tyr
1               5                   10                  15

Asp Thr Pro Arg Met Val Leu Val Arg Asn Lys Lys Val Gly Val Ile
            20                  25                  30

Phe Arg Leu Ile Gln Leu Val Val Leu Val Tyr Val Ile Gly Trp Val
        35                  40                  45

Phe Leu Tyr Glu Lys Gly Tyr Gln Thr Ser Ser Gly Leu Ile Ser Ser
    50                  55                  60

Val Ser Val Lys Leu Lys Gly Leu Ala Val Thr Gln Leu Pro Gly Leu
65                  70                  75                  80

Gly Pro Gln Val Trp Asp Val Ala Asp Tyr Val Phe Pro Ala Gln Gly
                85                  90                  95

Asp Asn Ser Phe Val Val Met Thr Asn Phe Ile Val Thr Pro Lys Gln
            100                 105                 110

Thr Gln Gly Tyr Cys Ala Glu His Pro Glu Gly Gly Ile Cys Lys Glu
        115                 120                 125

Asp Ser Gly Cys Thr Pro Gly Lys Ala Lys Arg Lys Ala Gln Gly Ile
    130                 135                 140

Arg Thr Gly Lys Cys Val Ala Phe Asn Asp Thr Val Lys Thr Cys Glu
145                 150                 155                 160

Ile Phe Gly Trp Cys Pro Val Glu Val Asp Asp Asp Ile Pro Arg Pro
                165                 170                 175

Ala Leu Leu Arg Glu Ala Glu Asn Phe Thr Leu Phe Ile Lys Asn Ser
            180                 185                 190

Ile Ser Phe Pro Arg Phe Lys Val Asn Arg Arg Asn Leu Val Glu Glu
        195                 200                 205

Val Asn Ala Ala His Met Lys Thr Cys Leu Phe His Lys Thr Leu His
    210                 215                 220

Pro Leu Cys Pro Val Phe Gln Leu Gly Tyr Val Val Gln Glu Ser Gly
225                 230                 235                 240

Gln Asn Phe Ser Thr Leu Ala Glu Lys Gly Gly Val Val Gly Ile Thr
                245                 250                 255

Ile Asp Trp His Cys Asp Leu Asp Trp His Val Arg His Cys Arg Pro
            260                 265                 270

Ile Tyr Glu Phe His Gly Leu Tyr Glu Glu Lys Asn Leu Ser Pro Gly
        275                 280                 285

Phe Asn Phe Arg Phe Ala Arg His Phe Val Glu Asn Gly Thr Asn Tyr
    290                 295                 300

Arg His Leu Phe Lys Val Phe Gly Ile Arg Phe Asp Ile Leu Val Asp
305                 310                 315                 320
```

-continued

```
Gly Lys Ala Gly Lys Phe Asp Ile Ile Pro Thr Met Thr Thr Ile Gly
                325                 330                 335

Ser Gly Ile Gly Ile Phe Gly Val Ala Thr Val Leu Cys Asp Leu Leu
            340                 345                 350

Leu Leu His Ile Leu Pro Lys Arg His Tyr Tyr Lys Gln Lys Lys Phe
        355                 360                 365

Lys Tyr Ala Glu Asp Met Gly Pro Gly Ala Ala Glu Arg Asp Leu Ala
    370                 375                 380

Ala Thr Ser Ser Thr Leu Gly Leu Gln Glu Asn Met Arg Thr Ser
385                 390                 395


<210> SEQ ID NO 3
<211> LENGTH: 18
<212> TYPE: DNA
<213> ORGANISM: Homo sapiens

<400> SEQUENCE: 3

gaaaagccca tgacaccc                                                    18


<210> SEQ ID NO 4
<211> LENGTH: 18
<212> TYPE: DNA
<213> ORGANISM: Homo sapiens

<400> SEQUENCE: 4

caacacggga cagagaac                                                    18


<210> SEQ ID NO 5
<211> LENGTH: 18
<212> TYPE: DNA
<213> ORGANISM: Homo sapiens

<400> SEQUENCE: 5

gatgtggtgc tggtcttg                                                    18


<210> SEQ ID NO 6
<211> LENGTH: 20
<212> TYPE: DNA
<213> ORGANISM: Homo sapiens

<400> SEQUENCE: 6

gctggcatct ctatccccca                                                  20


<210> SEQ ID NO 7
<211> LENGTH: 20
<212> TYPE: DNA
<213> ORGANISM: Homo sapiens

<400> SEQUENCE: 7

ggaactcaga gcctccttcc                                                  20


<210> SEQ ID NO 8
<211> LENGTH: 20
<212> TYPE: DNA
<213> ORGANISM: Homo sapiens

<400> SEQUENCE: 8

ggcaagatgg agctctggcc                                                  20


<210> SEQ ID NO 9
<211> LENGTH: 20
```

-continued

```
<212> TYPE: DNA
<213> ORGANISM: Homo sapiens

<400> SEQUENCE: 9

ggaactcaga gcctccttcc                                                    20


<210> SEQ ID NO 10
<211> LENGTH: 20
<212> TYPE: DNA
<213> ORGANISM: Homo sapiens

<400> SEQUENCE: 10

ggcaagatgg agctctggcc                                                    20
```